United States Patent [19]

Wild

[11] Patent Number: 5,598,860

[45] Date of Patent: Feb. 4, 1997

[54] DEVICE FOR CLEANING CONTACT LENSES

[75] Inventor: Patricia Wild, Onchan, Great Britain

[73] Assignee: Zygi Limited, Isle of Man, United Kingdom

[21] Appl. No.: 446,067

[22] Filed: May 19, 1995

[30] Foreign Application Priority Data

May 19, 1994 [GB] United Kingdom ............... 9410020

[51] Int. Cl.⁶ ........................................ B08B 3/04
[52] U.S. Cl. .................... 134/95.1; 134/901; 137/572
[58] Field of Search .............................. 134/901, 60, 91, 134/92, 95.1; 137/571, 572, 575

[56] References Cited

U.S. PATENT DOCUMENTS

| | | | |
|---|---|---|---|
| 1,174,674 | 3/1916 | Byer | 137/575 X |
| 1,204,078 | 11/1916 | Skidd | 137/571 X |
| 1,244,704 | 10/1917 | Coburn | 137/575 |
| 3,589,389 | 6/1971 | Nilsson | 137/571 X |
| 4,428,145 | 1/1984 | Wheeler | 137/575 X |
| 4,986,290 | 1/1991 | Oguma et al. | 134/901 X |
| 5,105,841 | 4/1992 | Oguma et al. | 134/901 X |
| 5,421,353 | 6/1995 | Jakubowski | 134/95.1 X |

FOREIGN PATENT DOCUMENTS 2230352 10/1990 United Kingdom .

*Primary Examiner*—Philip R. Coe
*Attorney, Agent, or Firm*—Young & Thompson

[57] ABSTRACT

A device for cleaning contact lenses comprises three liquid containers removably mounted one above another on a support. Each container has a liquid inlet and the two upper containers each have a liquid outlet, controlled by a valve in communication with the inlet of the container below it. In use, contact lenses are initially immersed in sterilizing solution in the middle container, and the upper container contains neutralizing solution. After a preset interval, a timed valve control device on the support operates the valves in sequence to discharge the sterilizing solution from the middle container into the lower container, and replace it with sterilizing solution from the upper container.

7 Claims, 1 Drawing Sheet

DEVICE FOR CLEANING CONTACT LENSES

BACKGROUND OF THE INVENTION

The invention relates to devices for cleaning contact lenses.

As is well known, contact lenses normally require, at intervals, to spend a period immersed in a sterilising solution. Typically, the user will store the lenses in an appropriate solution overnight. There are available one-step solutions where the lenses are placed in the solution at night, preferably after cleaning, and are simply removed from the solution and inserted in the eyes in the morning.

However, a two-step method is often considered to be superior, where the lenses are placed in a sterilising solution, typically hydrogen peroxide solution, following which the lenses are immersed in a neutralising solution. Although lenses are usually immersed in the sterilising solution overnight, one advantage of the two-step method is that the sterilising step can take as little as 30 minutes, followed by the neutralisation step of 10 minutes or so. As well as the two-step method being preferred, it may also be the only method available to someone who is allergic to some extent to solutions used in the one-step method.

However, the preferred two-step method currently has the disadvantage that it is inconvenient for the user to have to remove the lenses from the sterilising solution, introduce them into a neutralising solution, and then wait while the neutralisation takes place. Often the sterilisation is carried out overnight and the neutralisation step must be carried out in the morning before the user can insert the lenses into the eyes. It is therefore fairly common for the lenses to be left for insufficient time in the neutralising solution or even, in some cases, for the neutralising step to be omitted entirely. The result of inserting an un-neutralised lens into the eye can be very painful leading to irritation which can last for many hours.

The present invention sets out to provide a contact lens cleaning device where a required sequence of immersions, such as the two-step method referred to above, can be carried out automatically, with appropriate time delays, so that the lenses have completed their treatment and are available for use when required by the user.

SUMMARY OF THE INVENTION

According to the invention there is provided a device for cleaning contact lenses comprising a support structure, three liquid containers having means for mounting them at different levels on the support structure, each container having a liquid inlet and at least the two upper containers each having a liquid outlet, controlled by a valve, in communication with the inlet of the container at a level below it, and timed valve control means on the support structure for operating said valves in a predetermined timed sequence to control the flow of liquid between the containers in a desired manner.

Thus, for example, the above described two-step method may conveniently be carried out by the device according to the invention. In this case the upper container is filled with neutralising liquid, the intermediate container contains the lenses and is filled with sterilising solution, and the lower container is empty. After a predetermined sterilising period, the valves are automatically operated so that the sterilising solution is discharged from the intermediate container into the lower container and neutralising solution from the upper container is then discharged into the intermediate container containing the lenses. The timing may be so arranged that by the time the user requires to insert the lenses they have completed both sterilisation and the required period of immersion in the neutralising solution.

Although the invention does not exclude arrangements where the solutions are pumped from one container to another, preferably the locations of the containers, and the communications between them, are such that liquid flows by gravity from a container to a container at a level below it. In this case each container may be located directly above the container next below it. Each valve-controlled liquid outlet may be located above the liquid inlet of the container next below it so that liquid emerging from the outlet falls directly into the inlet below it. Preferably the inlet is larger than the outlet, and may for example comprise the open top of the container.

The containers may be detachably mounted on the support structure. In this case the mounting means are preferably arranged to orientate each container automatically in a position where its outlet control valve is operable by said valve control means.

Each outlet valve may have a movable operating member which is engageable by the plunger of a solenoid forming part of the valve control means. The movable operating member of each outlet valve may comprise a push rod, longitudinal movement of which moves a valve head into and out of engagement with a valve seat.

One of the containers may be detachably mounted on the support structure, each other container being detachably mounted on the next adjacent container. Preferably it is the lowermost container which is detachably mounted on the support structure, the other containers being detachably mounted in sequence above it.

Preferably at least one of the containers incorporates means for supporting a contact lens holder within the container.

The valve control means preferably comprise electrical circuitry, including electronic timing means, located in the support structure.

Although at least three containers are provided, the invention includes within its scope arrangements in which more than three intercommunicating containers are provided, for use in cases where more than two lens immersion steps may be required.

DETAILED DESCRIPTION OF THE PREFERRED EMBODIMENT

The contact lens cleaning device comprises a support structure including a flat base 10 from one side of which extends an upright housing 11. Three cylindrical open-topped containers 12, 13 and 14 are supported on the base 10 to one side of the housing 11. The containers are preferably moulded from transparent plastics material.

Figure 2:
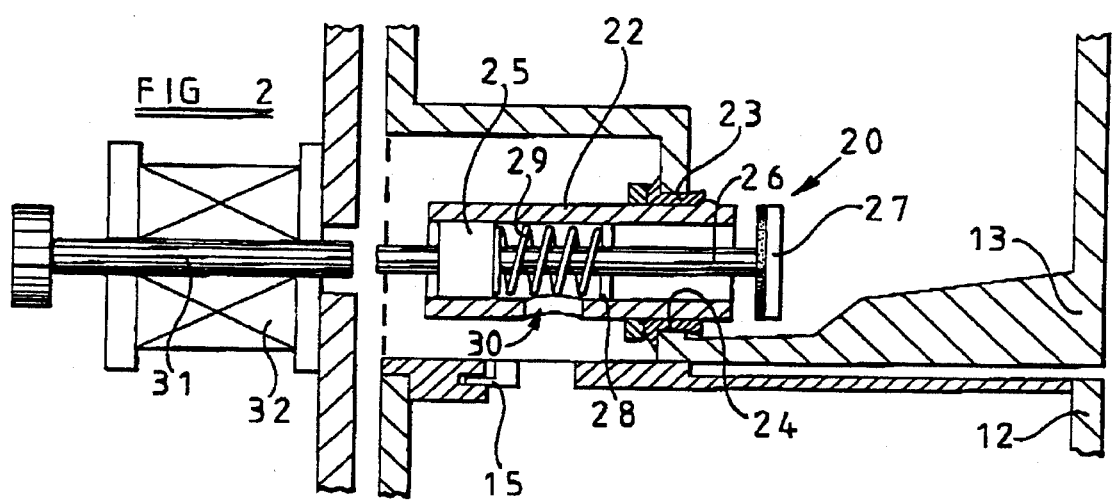
FIG. 2 is a diagrammatic view, on an enlarged scale, through an outlet valve and bayonet connection on one of the containers.

The lowermost container 12 is detachably secured to the base 10 by a rotatable bayonet fitting (not shown) which is asymmetrical so that the container 12 is always fitted to the base 10 in the same rotational orientation. A similar asymmetric bayonet fitting, indicated diagrammatically at 15 in FIG. 2, is also provided between the bottom of the intermediate container 13 and the open top of the lower container 12. A further similar bayonet connection is provided between the uppermost container 14 and the open top of the intermediate container 13. A removable cap 16 is fitted over the open top of the uppermost container 14.

The intermediate container 13 is provided with internal supports 17 for supporting a lens basket indicated diagrammatically at 18. The lowermost container 12 is provided with similar supports 19 so that the lens basket 18 may be placed in the container 12 if required.

The containers 13 and 14 are provided with valves 20 and 21 respectively. The valves are similar and the valve 20 will be described in greater detail with reference to FIG. 2.

Referring to FIG. 2; the valve 20 comprises a cylinder 22 one end of which is friction fitted, in fluid-type manner, in a plastics collar 23 in an aperture 24 in a wall of the container 13.

Slidable within the cylinder 22 is a piston 25 through which extends a push rod 26. A circular valve head 27 is formed on the end of the push rod 26 remote from the piston 25 and may be brought into and out of sealing engagement with the end of the cylinder 22.

The push rod 26 slides through an aperture in a fixed open spider 28 which extends across the cylinder 22, and a stainless steel compression spring 29 is disposed between the spider 28 and the piston 25 so as to urge the piston and push rod 26 to the left in FIG. 2, to a position where the valve head 27 sealingly engages the end of the cylinder 22 and closes off the outlet aperture 24 leading from the container 13.

A downwardly facing aperture 30 is formed in the side wall of the piston 22 and is disposed over the open top of the container 12.

The spring 29 normally biases the valve leftwards to the closed position and the valve is operated by the plunger 31 of a solenoid 32 mounted within the housing 11.

The arrangement is such that when the solenoid 32 is energised the plunger 31 is extended, i.e. is displaced to the right as seen in FIG. 2, and accordingly moves the push rod 26 to the right also, thus opening the valve 20.

A similar solenoid 33 (see FIG. 1) is arranged to operate the valve 21 in the upper container 14.

The solenoids 32 and 33 are controlled by electronic circuitry on a printed circuit board 34 mounted within the housing 11. The circuit is powered by a battery indicated at 35 and operation is initiated by depressing a push button 36 at the top of the housing 11.

The circuitry is programmed to operate the valves 20 and 21 in a timed sequence, as will be described, and an adjustment device (not shown) such as a manually settable dial or other control may be provided to enable the periods of the timing sequence to be adjusted. The details of the electronic circuitry required to achieve this form of operation will be apparent to those skilled in the art, and will not be described in detail.

In use, the intermediate container 13 is filled with sterilising solution and the lens basket 18, containing the contact lenses, is immersed in it. The container 14 is filled with neutralising solution, and the container 12 remains empty.

Figure 1:
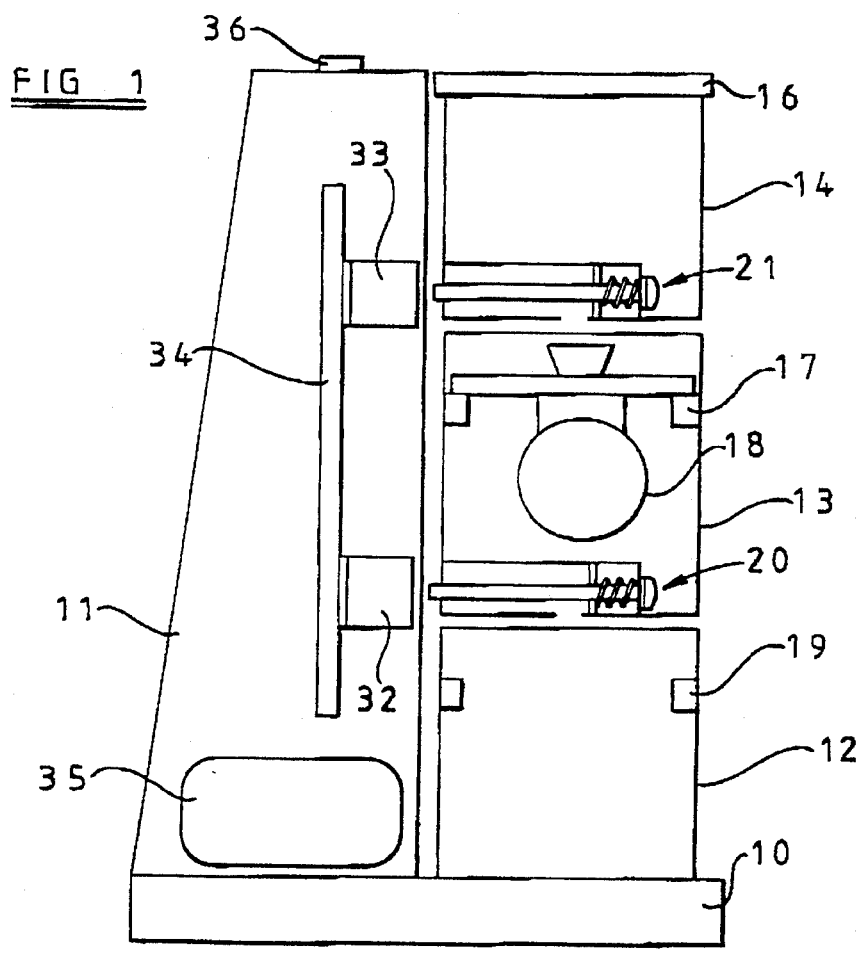
FIG. 1 is a diagrammatic vertical section through a contact lens cleaner in accordance with the invention.

The three containers are then mounted on the base 10, as shown in FIG. 1, using the aforementioned asymmetric bayonet fittings. The required timings are set, if a control for this is provided, and the button 36 is pressed to energise the circuit and initiate the timing.

Initially the valves 20 and 21 both remain closed. After a period of between 30 minutes and six hours, according to the setting of the timer, the solenoid 32 is automatically energised so as to open the valve 20 in the container 13. The sterilising solution in the container 13 thus drains through the apertures 24 and 30 into the empty container 12. The valve 20 remains open for an appropriate period, for example 10–15 seconds, sufficient to ensure that the container 13 is completely drained.

The valve 20 is then closed and the valve 21 in the upper container 14 is opened for a similar period by energisation of the solenoid 33. This drains the neutralising solution from the container 14 into the container 13. After an appropriate period, sufficient to effect neutralisation of the sterilising solution, the lenses are ready for use. A small indicating lamp may be provided on the housing 11 and arranged to be illuminated when an adequate neutralising period has elapsed.

Any malfunction of the device will be apparent since the lower container 12 will still be empty and the upper container 14 will still be full. The container 12 can be used for storage and transport of the lenses, when detached from the device, by mounting the lens basket 18 on the supports 19 and fitting a cover, such as the cover 16, to the top of the container.

The asymmetric bayonet fittings ensure that the three containers are always fitted one to another in the same correct orientation, so that the push rods 26 of the valves 20 and 21 are in the appropriate position for engagement by the solenoid plungers.

The containers may be marked to ensure that they are assembled in the correct order. For example they may be colour coded in the well known arrangement of traffic lights, i.e. the upper container 14 may be coloured red, the intermediate container 13 coloured amber and the lower container 12 coloured green.

I claim:

1. A contact lens cleaning device comprising a support structure, three liquid containers consisting of upper and lower containers and an intermediate container incorporating a contact lens holder, each of the containers having an open top and the upper and intermediate containers each having a valved outlet opening into the open top of the container immediately below, means for detachably mounting the containers one above the other on the support structure, and timed valve control means on the support structure for opening the valved outlets in a predetermined timed sequence to cause a first liquid, within which contact lenses supported by the contact lens holder are immersed, to flow by gravity from the intermediate container to the lower container in a first operating step, and subsequently to cause a second liquid to flow by gravity from the upper container to the intermediate container in a second operating step so as to immerse the contact lenses in the second liquid.

2. A device according to claim 1, wherein each outlet valve has a movable operating member which is engageable by the plunger of a solenoid forming part of the valve control means.

3. A device according to claim 2, wherein the movable operating member of each outlet valve comprises a push rod, longitudinal movement of which moves a valve head into and out of engagement with a valve seat.

4. A device according to claim 1, wherein one of the containers is detachably mounted on the support structure, each other container being detachably mounted on the next adjacent container.

5. A device according to claim 4, wherein the lowermost container is detachably mounted on the support structure, the other containers being detachably mounted in sequence above the lowermost container.

6. A device according to claim 1, wherein said intermediate container incorporates means for supporting a contact lens holder within the container.

7. A device according to claim 1, wherein the valve control means comprise electrical circuitry, including electronic timing means, located in the support structure.

* * * * *